United States Patent [19]
Walters et al.

[11] Patent Number: 6,029,498
[45] Date of Patent: Feb. 29, 2000

[54] CHROMATOGRAPHIC COLUMN FOR MICROWAVE HEATING

[75] Inventors: David L. Walters, Northglenn; Scott Gaisford, Denver, both of Colo.

[73] Assignee: MT Systems, LLC, Denver, Colo.

[21] Appl. No.: 09/342,368

[22] Filed: Jun. 29, 1999

Related U.S. Application Data

[63] Continuation-in-part of application No. 09/108,297, Jul. 1, 1998.

[51] Int. Cl.⁷ .................................................. G01N 30/02
[52] U.S. Cl. ........................... 73/23.39; 73/23.35; 95/82; 95/87; 422/88
[58] Field of Search ................................ 73/23.35, 23.39; 95/82, 87, 88; 422/88, 89

[56] References Cited

U.S. PATENT DOCUMENTS

| | | |
|---|---|---|
| 3,023,835 | 3/1962 | Brashear . |
| 3,169,389 | 2/1965 | Green, Jr. et al. . |
| 3,232,093 | 2/1966 | Burow et al. . |
| 3,527,567 | 9/1970 | Philyaw et al. . |
| 4,204,423 | 5/1980 | Jordan ..................................... 73/23.39 |
| 4,347,216 | 8/1982 | Kawasaki et al. . |
| 4,861,556 | 8/1989 | Neas et al. . |
| 4,882,286 | 11/1989 | Neas et al. . |
| 4,904,450 | 2/1990 | Floyd . |
| 5,005,399 | 4/1991 | Holtzclaw et al. . |
| 5,066,843 | 11/1991 | Revesz . |
| 5,314,664 | 5/1994 | Sperling et al. . |
| 5,377,426 | 1/1995 | Parë . |
| 5,427,741 | 6/1995 | Bennett . |
| 5,443,795 | 8/1995 | Revesz . |
| 5,447,052 | 9/1995 | Delaune et al. . |
| 5,509,956 | 4/1996 | Opperman et al. . |
| 5,519,947 | 5/1996 | Parë . |
| 5,675,909 | 10/1997 | Parë . |
| 5,808,178 | 9/1998 | Rounbehler et al. ................... 73/23.39 |

FOREIGN PATENT DOCUMENTS

| | | | |
|---|---|---|---|
| 61-68561 | 4/1986 | Japan .................................... | 73/23.39 |
| 186759 | 10/1966 | U.S.S.R. .............................. | 73/23.39 |

*Primary Examiner*—Daniel S. Larkin
*Attorney, Agent, or Firm*—Dorr, Carson, Sloan & Birney, P.C.

[57] ABSTRACT

A chromatography column for microwave heating either incorporates microwave absorbing material into the column itself or positions the column adjacent to microwave absorbing material so that the column and the chromatography sample contained therein are heated by the microwave absorbing material via conduction or convection. For example, a microwave absorbing material (e.g., ferrite) can be fused into the inner silica layer or incorporated in an outer polymer layer of the column. Microwave absorbing material can also be incorporated into an external element (e.g., an outer tube, sleeve, or spool) positioned adjacent to the chromatography column. A layer of thermal insulation can be placed around the column to decrease the rate of heat loss. Optionally, a gap can be provided between the chromatography column and thermal insulation to further reduce heat loss during the heating cycle and to accelerate cooling at the end of the heating cycle by making it possible to ventilate the heated column. The chromatography column assembly can be protected from overheating by selecting a microwave absorbing material having a loss factor that decreases rapidly above a predetermined maximum temperature.

20 Claims, 7 Drawing Sheets

CHROMATOGRAPHIC COLUMN FOR MICROWAVE HEATING

RELATED APPLICATION

The present application is a continuation-in-part of the Applicants' co-pending U.S. patent application Ser. No. 09/108,297, entitled "Chromatographic Column For Microwave Heating," filed on Jul. 1, 1998.

BACKGROUND OF THE INVENTION

1. Field of the Invention

The invention relates generally to the field of gas and liquid chromatography and specifically to the design of chromatographic column assemblies which facilitate the heating of chromatographic columns using microwave heating methods.

2. Statement of the Problem

Gas and liquid chromatography are physical methods for the separation, identification, and quantification of chemical compounds. These methods are used extensively for applications that include the measurement of product purity in analytical chemistry, the determination of environmental contamination, the characterization of natural substances, and the development of pharmaceuticals.

The fundamental methods used in gas and liquid chromatographs to separate chemical constituents are similar. A sample mixture is injected into a flowing neutral carrier stream and the combination then flows through a tube or chromatographic column. The inner surface of the column is coated or packed with a material called the stationary phase. As the sample mixture and carrier stream flow through the column, the components within the mixture are retained by the stationary phase to a greater or lesser degree depending on the relative volatility (in the case of gas chromatography) or the relative solubility (in the case of liquid chromatography) of the individual components and on their respective affinities for the stationary phase. When the individual mixture components are released into the carrier stream by the stationary phase, they are swept towards the column outlet where they are detected and measured with a detector. Different chemical compounds are retained for different times by the stationary phase. By measuring the retention times, the specific compounds in the mixture can be identified. The relative concentration of the compounds is determined by comparing the peak amplitudes measured with the detector for each compound. The primary difference between gas and liquid chromatography is the mode of separation. In gas chromatography, the sample is volatilized and propelled down the analytical column by a moving stream of gas. In liquid chromatography, the sample is dissolved and propelled down the analytical column in a moving stream of liquid. Another difference between gas and liquid chromatography is that the columns used in liquid chromatography are generally filled or packed with the stationary phase, while those used in gas chromatography can also have the stationary phase coated or bonded to the interior wall, instead.

GC and LC measurements are facilitated by the application of heat to the chromatographic column to change its temperature. The use of a heated column oven in gas chromatographic systems greatly increases the number of compounds that can be analyzed and speeds up the time required for each analysis by increasing the volatility of higher molecular weight compounds. Heating an LC column affects the relative solubility of the mixture's components in the two phases and can enhance the separation as well as improve the repeatability of the elution times of the component chemicals.

Many methods have been described for heating chromatographic columns. The simplest and most commonly used method utilizes resistive heating elements to heat air which is in turn circulated through an insulated oven in which the column is placed. For example, U.S. Pat. No. 3,527,567 to Philyaw et al. describes a GC oven heated with resistive elements.

The resistive element heating method has several limitations. To achieve even heating of the column, a large volume of air is rapidly circulated around the chromatographic column. In addition to heating the column, the air heats the oven itself. Because the thermal mass of the oven is much larger than that of the column, the rate at which the column can be heated is commensurately reduced. A related problem is cooling time. After heating the oven to a high temperature during an analysis, it takes significantly longer to cool the oven plus the column to their initial temperature so that the next sample may be analyzed than it would to cool the column alone. Together, these limitations reduce the throughput of the chromatograph.

Attempts to localize the resistive heat element onto the column itself so as to reduce or eliminate peripheral heating of the 'oven' are described in U.S. Pat. No. 3,169,389 to Green et al., U.S. Pat. No. 3,232,093 to Burow et al., and in U.S. Pat. No. 5,005,399 to Holtzclaw et al. Each of these patents describe methods for directly wrapping or cladding the chromatographic column with a resistive heating element. Methods are also described for positioning the resulting metal clad column adjacent to a cooling source to decrease cooling times. This method of heating can be difficult to implement in practice because of uneven heating of the column due to local hot or cold spots in the resistive heating element surrounding the column. Uneven heating of the column in turn compromises the quality of the analysis.

Yet another limitation of all resistively heated chromatographic devices is that if operated improperly, they can be driven to temperatures higher than the maximum tolerated by a given column resulting in damage to or destruction of the column.

An alternative method for heating chromatographic columns is microwave heating as described in U.S. Pat. No. 4,204,423 to Jordan. Potential advantages of microwave heating are efficiency and selectivity. Suitable objects placed in a microwave oven will be heated when the oven is operated, but the temperature of the oven itself will not change. Microwave heating occurs in materials which absorb the microwave energy and convert it into heat. Current chromatographic columns are generally made of materials that do not absorb microwave energy at an appreciable rate. For example, most GC capillary columns are made of polyimide and fused silica. Consequently, such columns will not heat at an appreciable rate when placed in a microwave oven. The apparatus taught by Jordan is not practicable with these columns.

Jordan teaches that any column material can be placed in a microwave oven except for conductive materials such as metals which will reflect the electromagnetic energy (by shorting out the electric field) in the microwave oven, thus rendering it inoperable. Indeed any such non-metal material can be placed in a microwave oven, but they will not necessarily be heated by the oven.

U.S. Pat. No. 3,023,835 to Brashear describes an apparatus for heating packed chromatographic columns by exposing them to radio frequency (RF) radiation. Brashear describes heating chromatographic columns via dielectric heating or via inductive heating (i.e., magnetic heating). In the case of dielectric heating, Brashear specifies that the column and the packing filler are constructed of electrically insulating materials. Most insulating materials, including those used to make chromatographic columns, do not absorb electromagnetic energy at a high enough rate to make dielectric heating as taught by Brashear practical. In the case of inductive heating, Brashear specifies that: (1) the column is constructed of a metal containing some magnetic components to enable inductive heating to occur; (2) the filler contains a metal powder to promote heat conduction from the column into the filler; and (3) the metal powder may also be magnetic to promote local inductive heating. In practice, inductive heating of the filler would not occur inside the metal column because it would be shielded from the electromagnetic field by the metal column in which it is sheathed. Moreover, metal-filled packing material inside columns is not generally a good scheme. The sample material passing down the column can be exposed to the metal. If the metal is not chemically inert, then some components of the sample can react with the metal thus distorting the resulting chromatogram.

Neither of the packed column constructions described by Brashear would be of practical usage in a microwave heating apparatus as taught by Jordan where the whole of the column is placed inside a cavity and exposed to high intensity electromagnetic radiation. The insulating low-loss column would not heat rapidly enough to be of practical use. The metal column would short out the electric field to such a significant extent that the microwave oven would not function properly and the column, if heated at all, would not be heated evenly.

3. Solution to the Problem

Microwave heating occurs in materials having dielectric or magnetic loss factors sufficiently high that when exposed to high frequency electromagnetic radiation these materials absorb sufficient energy from the electric or magnetic field to heat at an appreciable rate. Materials with high dielectric loss factors absorb energy from electric fields. Conversely, materials with high magnetic loss factors absorb energy from magnetic fields. Microwave heating apparatuses have both electric and magnetic fields within them so either loss mechanism will result in heating.

Food is heated well in microwave ovens because it contains water. Water has a high dielectric loss factor at microwave frequencies and is thus readily heated by energy absorbed from the electric field. The water in turn heats the rest of material in the food through conventional heat conduction and convection mechanisms. In order for a GC or an LC column to be heated in a microwave heating apparatus, it too must contain or be adjacent to a material which absorbs electromagnetic energy through dielectric or magnetic loss mechanisms. This material can then heat the column.

Chromatographic columns can be modified in one of two ways to make microwave heating practical. First, the column itself can be modified to incorporate a microwave absorbing material such that direct heating of the column is achieved. Second, the column can be positioned adjacent to (i.e., in contact with, or in close proximity to) a microwave absorbing material in an assembly that provides adequate heat transfer so that the column is heated by the microwave absorbing material via conduction or convection.

By carefully selecting the microwave absorbing material (s) used in chromatographic columns assemblies, intrinsic over-temperature protection can be built into the column so that it cannot be heated in a microwave heating apparatus to a temperature beyond a desired maximum temperature. Dielectric and magnetic loss factors are usually temperature dependent. If a microwave absorbing material is selected for which the loss factor decreases rapidly at the maximum desired column temperature, then the column assembly using this material cannot be heated appreciably above the desired temperature in a microwave heating apparatus. One way to achieve this is to select a ferromagnetic absorbing material having the correct Curie temperature. The loss factor of a ferromagnetic absorber decreases dramatically at its Curie temperature.

As compared to conventional resistively heated chromatographic systems, a microwave-absorbing column assembly heated in a microwave apparatus can be heated much more quickly and efficiently and subsequently cooled more quickly because: (1) the total thermal mass of the material to be heated or cooled is much smaller than in a conventional oven; and (2) the microwave energy selectively heats the desired material and not the whole of the oven.

Because the thermal mass of a microwave-absorbing column assembly is so small it could easily lose significant fractions of its heat to the environment while it is being heated. This undesired heat flow can limit the heating rate of the column and in some circumstances the cooling rate as well. To help control this heat flow, microwave-absorbing columns assemblies can be enclosed in insulating materials to better isolate them thermally from their environment. Standard chromatograph columns are not insulated in this manner from the oven environment. Materials used to insulate a microwave absorbing column assembly must be selected so as not to disturb the heating of the column by the microwave heating apparatus. To allow the heat to escape from the column when cooling is desired, the column insulator can be designed to allow air or some other heat sink material to be circulated around the column when needed to cool the column assembly.

SUMMARY OF THE INVENTION

The present invention provides a chromatography column for microwave heating that either incorporates microwave absorbing material into the column itself or positions the column adjacent to microwave absorbing material so that the column and the chromatography sample contained therein are heated by the microwave absorbing material via conduction, convection or radiation. For example, a microwave absorbing material (e.g., ferrite, iron, cobalt, nickel, or carbon) can be fused into the inner silica layer or incorporated in an outer polymer layer of the column. Microwave absorbing material can also be incorporated into an external element (e.g., an outer tube, sleeve, or spool) positioned adjacent to the chromatography column. A layer of thermal insulation can be placed around the column to decrease the rate of heat loss to the column's surroundings. Optionally, a gap can be provided between the chromatography column and thermal insulation to further reduce heat loss during the heating cycle and accelerate cooling at the end of the heating cycle by making it possible to ventilate the heated column. The chromatography column assembly can be protected from overheating by selecting a microwave absorbing material having a loss factor that decreases rapidly above a predetermined maximum temperature.

It is the object of the invention to provide a chromatographic column assembly which can be rapidly and efficiently heated and rapidly cooled in a microwave heating apparatus.

It is the object of the invention to provide a chromatographic column assembly which together with a microwave heating apparatus provides improved heating and cooling rates as compared to conventional resistively heated chromatographic ovens.

It is the object of the invention to provide a chromatographic column assembly which together with a microwave heating apparatus provides for more efficient heating than with conventional resistively heated chromatographic ovens.

It is the object of the invention to provide a chromatographic column containing a dielectric or magnetic absorbing material such that the column can be heated by a microwave heating apparatus.

It is the object of the invention to provide a chromatographic column assembly containing a chromatographic column and a dielectric or magnetic absorbing material where the column is held adjacent to the microwave-absorbing material such that the two are kept in close thermal contact and the column is heated by the microwave-absorbing material via conduction or convection when the microwave-absorbing material is heated in a microwave heating apparatus.

It is the object of the invention to provide a chromatographic column assembly designed to prevent the column from reaching an excessive temperature in a microwave heating apparatus by selection of a microwave absorbing material for which the absorbing properties decrease with increasing temperature to an extent that it stops heating effectively beyond a certain temperature.

It is the object of the invention to provide a chromatographic column assembly designed to prevent the column from reaching an excessive temperature in a microwave heating apparatus by selection of a magnetic absorbing material having a Curie temperature low enough to prevent the absorber from reaching a temperature in excess of the maximum desired column temperature.

It is the object of the invention to provide means of controlling the flow of heat from a microwave-absorbing column assembly.

These and other advantages, features, and objects of the present invention will be more readily understood in view of the following detailed description and the drawings.

BRIEF DESCRIPTION OF THE DRAWINGS

The present invention can be more readily understood in conjunction with accompanying drawings, in which.

DETAILED DESCRIPTION OF THE INVENTION

Microwave heating can occur in a material if its dielectric or magnetic loss factor is significantly greater than zero. When such a material is exposed to a high frequency electric or magnetic field, the material will absorb power from the field and convert this power into heat. The average power per unit volume absorbed by a given material is described by the following equation:

$$P_{av} = \omega \epsilon_o \epsilon''_{\textit{eff}} E_{rms}^2 + \omega \mu_o \mu''_{\textit{eff}} H_{rms}^2 \quad (1)$$

where $\omega$ is the angular frequency of the electromagnetic radiation, $\epsilon_o$ is the permittivity of free space, $\epsilon''_{\textit{eff}}$ is the dielectric loss factor, $E_{rms}$ is the rms electric field strength, $\mu_o$ is the permeability of free space, $\mu''_{\textit{eff}}$ is the magnetic loss factor, and $H_{rms}$ is the rms magnetic field strength.

The dielectric loss factor $\epsilon''_{\textit{eff}}$ is a parameter which describes losses associated with the movement of electrical charge in a material; i.e. conduction losses. There are two distinct sources of conduction losses. The first is associated with very short range electrical currents called displacement currents that result from the rotation of permanent dipoles within a material in response to an electric field. The second source of conduction loss is associated with long range charge transport within a dielectric material that is somewhat conductive. For the purposes of this description, the dielectric loss factor includes all electrical losses associated with the conduction of electrical charge through a material in response to an electric field.

The material will heat at a rate in ° C./sec given by:

$$\text{Heating Rate} = P_{av}/\rho c_p \quad (2)$$

where $\rho$ is the density of the material, and $c_p$ is the specific heat of the material, As shown by equations (1) and (2), the rate at which the temperature of a material will heat when exposed to microwave radiation is proportional to the dielectric and magnetic loss factors of the material.

Table 1 summarizes the properties of some materials at 25° C. and at a frequency of 2.5 GHz, which is a frequency commonly used for microwave heating.

TABLE 1

| Material | $\epsilon''_{eff}$ | $\mu''_{eff}$ | ρ(g/cc) | $c_p$(J/g °C.) |
|---|---|---|---|---|
| Silica Glass | 0.0004 | 0.0 | 2.2 | 0.75 |
| Polyimide | <0.008 | 0.0 | 1.4 | 1.67 |
| Air | <0.0001 | 0.0 | — | 1.0 |
| Polytetra-fluoroethylene | <0.0003 | 0.0 | 2.15 | — |
| Silicone Rubber | 0.05 | 0.0 | 1.15 | 2.0 |
| Fresh Water | 9.5 | 0.0 | 1.0 | 4.18 |
| Alumina | <0.01 | 0.0 | 3.9 | 0.92 |
| Ferrite (Crowley 20 from H.L. Crowley) | 0.54 | 2.5 | — | — |
| Iron-Filled Epoxy (Eccosorb CRS 124 from Emerson & Cuming) | 1.9 | 2.55 | 4.55 | 2.92 |

Figure 1:
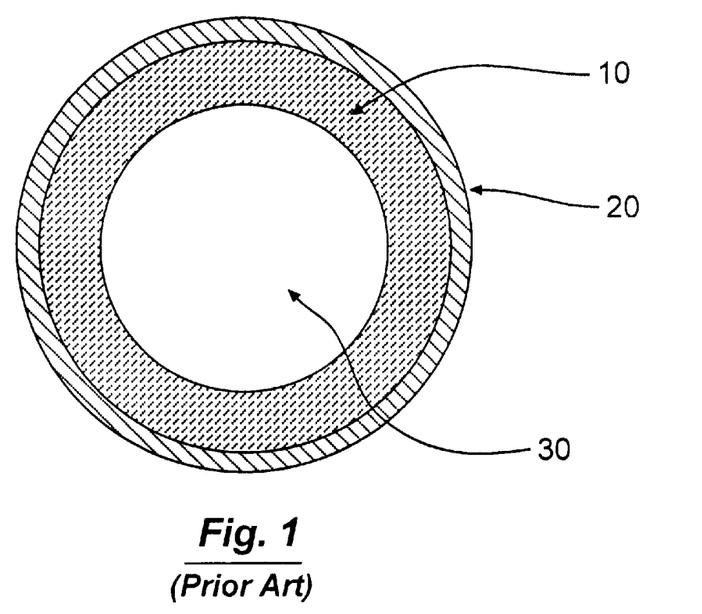
FIG. 1 shows the cross section of a typical chromatograph column.

FIG. 1 shows the cross section of the most common type of GC capillary column. It is a tube fabricated of fused silica (glass) 10 coated externally with polyimide 20 for added strength. The fused silica has an ID ranging from 0.1 to 0.53 mm in diameter. The wall thickness of the fused silica is 0.1 to 0.2 mm. The wall thickness of the polyimide is typically about 5 μm. The interior 30 of tube 10 consists of a thin stationary phase of typically 1 μm or less that is bonded to the inside of the fused silica (not shown in FIG. 1) and the remainder is gas most of which is the inert carrier gas. The total length of the capillary column varies typically from 15 to 60 m.

An LC column generally consists of a metal or plastic tube packed with a porous support material such as crushed silica to which is bound a stationary phase. Tube dimensions generally range from an internal diameter of 1 mm to 10 mm and a length of 5 cm to 30 cm. Taking FIG. 1 as an LC column, element 10 is the tube and element 30 is the packed support material and stationary phase. The external coating 20 is not used with a LC column.

The major non-metal components of these columns are crushed or fused silica glass, polyimide, and plastic. As indicated in Table 1, these materials have very low dielectric and magnetic loss factors. Most plastics and glasses have loss factors less than that shown for polyimide. If placed in a microwave heating apparatus and exposed to an electromagnetic field strength of equal intensity, these materials will absorb power at a rate about 1000 times slower than will water. It is not feasible to increase the electric field intensity enough to compensate for the low loss factors owing to dielectric breakdown problems. Consequently, it is not practical to heat standard chromatograph columns in microwave heating devices. To correct this limitation and to make the attractive aspects of microwave heating possible in chromatographic applications, appropriate high loss factor material(s) must be added to the columns or placed adjacent to them so that this material(s) will heat up when exposed to microwave radiation and then heat the column via heat conduction or convection.

Many types of high loss factor materials could be used to increase the heating rate of a chromatographic column in a microwave heating apparatus. High loss factor in this case means any material with a high enough loss factor to enable a chromatographic column to be heated at a rate of at least a few degrees Centigrade per minute and preferably at a rate of 100° C. per minute or more. Such a material would likely have a loss factor of at least 0.05. However, microwave absorbing materials having loss factors less than 0.05 can be used if they are heated in microwave heating apparatuses with very high quality factors. A microwave heating apparatus with a high quality factor will not itself absorb much microwave power. In general, the total microwave losses in a microwave absorbing material used to heat a column or column assembly in a microwave heating apparatus should be at least as great as the total losses that occur elsewhere in the microwave heating apparatus, such that the microwave heating apparatus is at least 50% efficient in delivering available microwave power in the microwave heating apparatus to the microwave absorbing material.

Microwave absorbing materials with high dielectric or magnetic loss factors could be used. Examples of materials with high dielectric loss factors include carbon and some forms of titanium oxide. Examples of materials with high magnetic loss factors include ferrites, iron, nickel, and cobalt. Carbon, iron, nickel, and cobalt are electrically conductive and as such not good microwave absorbing material candidates by themselves in a microwave heating application because they will tend to short out or distort the electromagnetic field in a microwave heating apparatus. However, when used as an additive in an electrically insulating material such as epoxy, rubber, or plastic, the resulting matrix typically has a much lower conductivity and so does not disable a microwave heating apparatus, yet retains a significant portion of the microwave absorbing characteristics of the additive. The iron-filled epoxy in Table 1 is such a mixture. Carbon-loaded materials are another example of such mixtures. In carbon-loaded mixtures, moderately conductive carbon is added to a dielectric material in precise quantities to give the resulting mixture a desired volume resistivity. Such mixtures are the basis for carbon-film resistors.

The term "microwave absorbing material" refers broadly to any material with a high enough dielectric or magnetic loss factor that can be heated in a microwave heating apparatus at a sufficiently fast rate and to a high enough temperature to be of practical value in gas or liquid chromatographic applications. This typically requires a loss factor of at least 0.05. "Microwave absorbing material" also includes materials such as iron or carbon that are electrically conductive and therefore are not good absorbers by themselves, but are good microwave absorbers when added in powdered form as fillers to nonconductive materials, such as epoxies or plastics. In such a mixture, it is the filler material that absorbs the microwave energy and is heated as a result. For such material matrices, the term "microwave absorbing material" refers to the filler material that actually absorbs the microwave energy, rather than to the matrix as a whole. It should be clear to one of ordinary skill in the art that "microwave absorbing material" refers to any material or combination of materials that can be used to significantly enhance microwave heating of a chromatographic column.

The term "microwave absorbing matrix" will be used to refer to mixtures of microwave absorbing materials and insulating materials. These material mixtures will often have specific advantages in chromatographic applications in that they overcome common physical limitations of most microwave absorbing materials by themselves. Gas chromatographic columns must typically be flexible, chemically inert, and capable of withstanding frequent temperature cycling. Similarly, liquid chromatographic columns must typically be chemically inert, and capable of withstanding high pressure and frequent temperature cycling. Few, if any microwave absorbing compounds or elements by themselves meet these requirements. However, when a microwave absorbing material is mixed into an insulating material with suitable physical properties, such as polyimide, the resulting mixture has physical properties similar to those of the insulating material yet absorbs microwave energy because of the microwave absorbing filler. Thus, microwave absorbing matrices can be engineered that combine good physical and microwave absorbing properties. Here again, the resulting material matrix should typically have an overall loss factor of at least 0.05. Preferred embodiments of such microwave absorbing matrices include mixtures of a high grade plastic such as polyimide or polyetherether ketone (PEEK) and an additive such as iron, ferrite, nickel, cobalt, or carbon. In the descriptions of the chromatographic column assemblies herein, the term "microwave" will also be used broadly to cover electromagnetic radiation in the frequency range from 10 MHz to 1000 GHz.

Chromatographic columns can be augmented with a microwave absorbing material in two ways to enhance the effectiveness of microwave heating devices in heating the columns. First, a microwave absorbing material can be added directly to a column resulting in direct conductive heating of the reminder of the column (e.g., a combination of a continuous phase material and the microwave absorbing material). Second, microwave absorbing material can be placed adjacent to (i.e., in thermal contact with, or in close proximity to) a column such that the column is heated indirectly by thermal conduction or convection. There are many arrangements of microwave absorbing material and a column which achieve one or both of these configurations.

Figure 2:
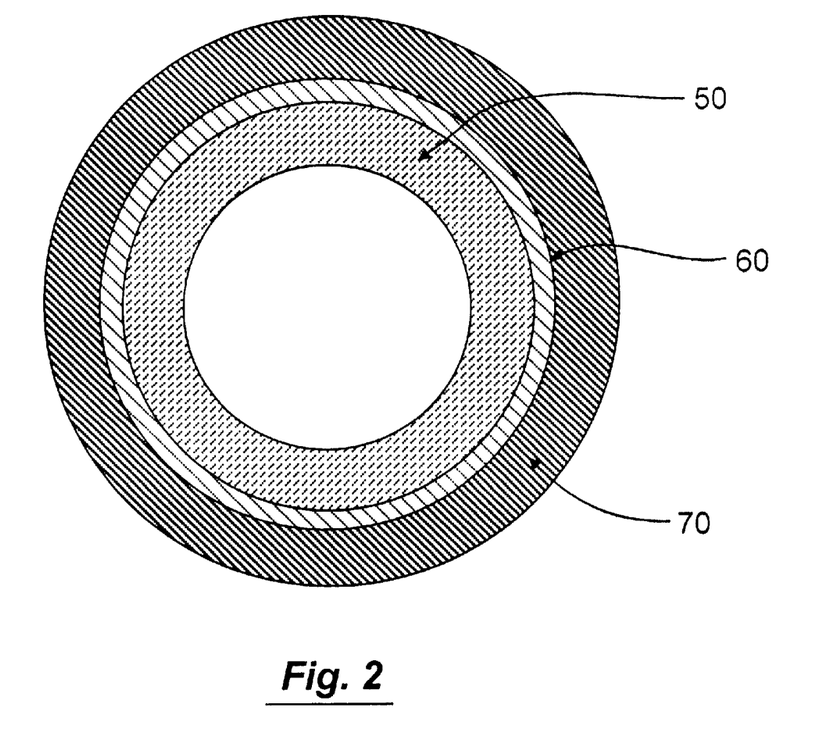
FIGS. 2 and 3 show the cross-sections of a two chromatograph columns with a microwave absorbing material added in accordance with the present invention.

Adding a Microwave Absorbing Material to a Column. FIG. 2 shows the cross section of a chromatographic column where an external layer 70 comprising microwave absorbing material is added to the outside of an existing column. For a fused silica or glass GC capillary column, tube 50 represents a fused silica or glass tube. It is coated with an optional layer of a polymer 60, such as polyimide. The polyimide layer 60 is optional for this modified chromatograph column because the microwave absorbing layer 70 could provide the same function as the polyimide layer in existing columns. For chromatographic columns other than fused silica or glass capillary columns, such as packed GC columns or an LC columns, tube 50 is a glass or plastic tube. Tube 50 could even be metal if the microwave absorbing material 70 shields it sufficiently to prevent the metal from short circuiting the electric field in a microwave heating apparatus. For columns with a glass, plastic, or metal tube 50, the polymer layer 60 would not be present.

Figure 3:
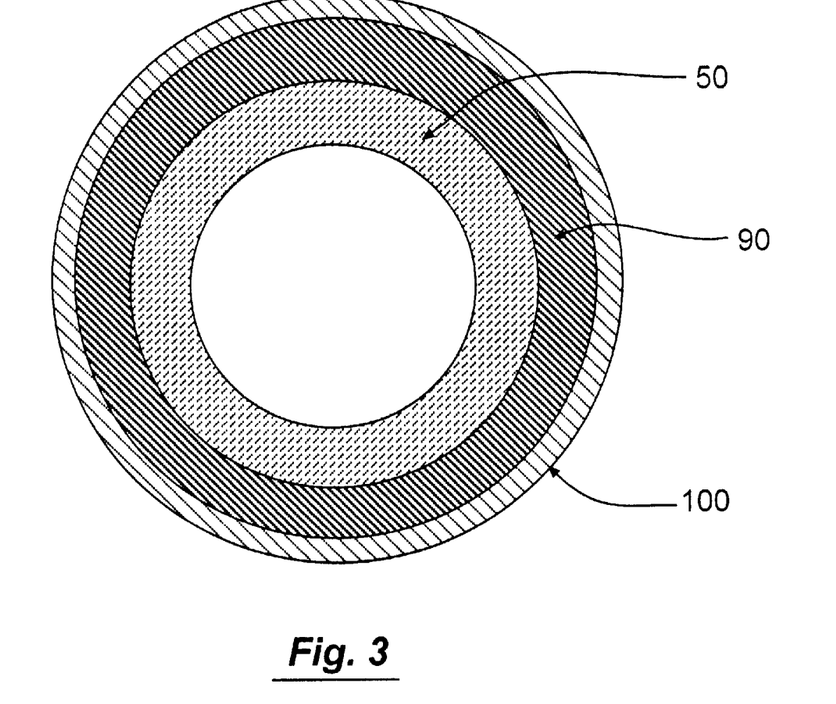

A better configuration is shown in FIG. 3. In this embodiment, a microwave absorbing material layer 90 is added to the existing chromatograph column tube 50. The tube 50 could be fused silica, glass, plastic, or metal. The polymer sheath 100 covers the outside of the microwave absorbing material 90. Together, the tube 50 and sheath 100 physically isolate the microwave absorbing layer 90 from the environment. Sheath 100 could consist of a material such as polyimide or polytetrafluoroethylene, sold under the trademark TEFLON.

Figure 4:
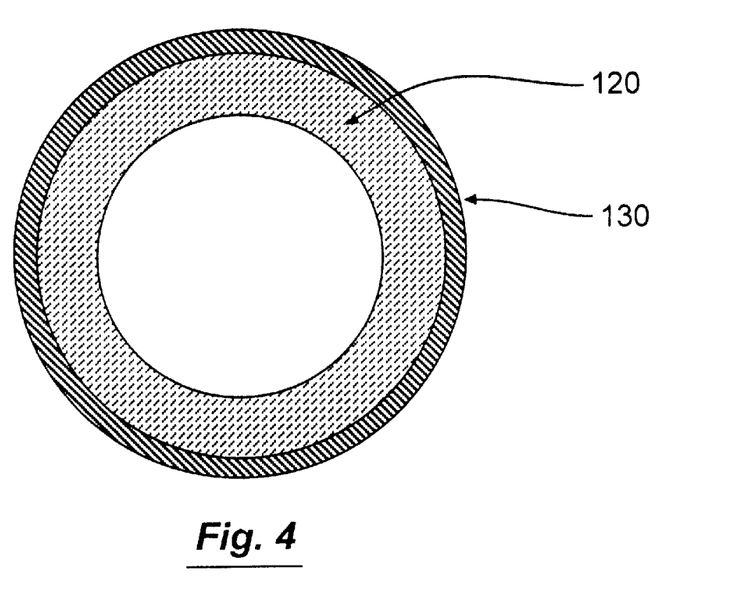
FIG. 4 shows the cross-section of a chromatograph column with a microwave absorbing material mixed into one of the existing column layers accordance with the present invention.

Another manner in which a microwave absorbing material can be added to a chromatographic column is to mix a microwave absorbing material into one of the materials already used in a column so as to make a microwave absorbing matrix. In FIG. 4, column tube 120 is a fused silica, glass, or plastic tube in which a microwave absorbing material has been mixed. The resulting microwave absorbing matrix can be readily heated in a microwave heating apparatus. Where applicable, tube 120 is coated with a thin layer 130 of material such as polyimide to strengthen and environmentally isolate the column.

Alternatively, the microwave absorbing material could be mixed into the outer polymer layer 130 rather than into the tube 120. The electrical effect on the column would be much the same. In effect, this structure is illustrated in FIG. 3 where the microwave absorbing layer 90 consists of a polyimide-microwave absorbing material mixture and the sheath 100 is absent. For example, the polyimide can be impregnated with iron, nickel, ferrite, carbon, or other microwave absorbing materials to form a composite material that can be readily extruded over the column during manufacture.

In another embodiment, an inner layer of fused silica, glass, or plastic is surrounded by an intermediate layer containing a microwave absorbing material. A polymer, such as polyimide, is then applied over the intermediate layer to form a third, outer layer that provides a degree of physical protection, thermal insulation, and added strength for the column assembly.

There are many different physical configurations with which a microwave absorbing material can be added to a chromatographic column so as to make it possible to heat the column in a microwave heating apparatus. The microwave absorbing material can be mixed into one of the column components or it can be bonded to the column as an exterior or interior layer. Some combination of these physical configurations could also be used. It should be clear to one of average skill in the art that the invention lies in the addition of the microwave absorbing material to an existing chromatographic column and not in the manner in which it is added.

Column Assemblies With A Microwave Absorbing Material Adjacent To A Column. A chromatographic column can be heated in a microwave heating apparatus by a microwave absorbing material if the column is located adjacent to the microwave absorbing material such that heat is transferred by the absorbing material to the column via thermal conduction, convection, or radiation. Ideally, the column assembly should keep the temperature difference between the microwave absorbing material and the column to a minimum.

Figure 5:
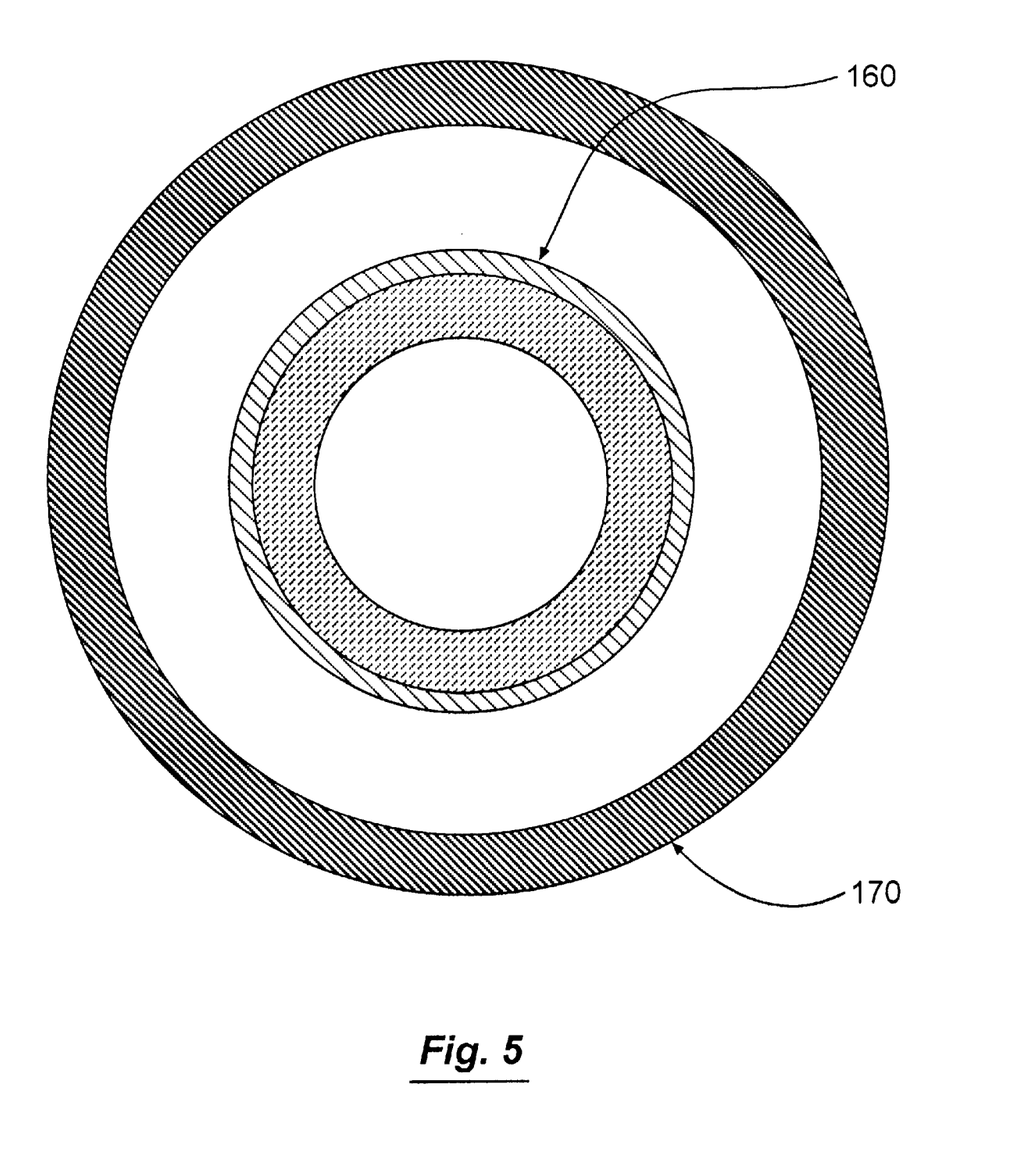
FIG. 5 shows the cross-section of a chromatograph column assembly constructed in accordance with the present invention where an existing column is inserted inside a second tube made at least in part with a microwave absorbing material.

FIG. 5 shows the cross-section of one column assembly built in accordance with the present invention. At least a portion of a standard chromatographic column 160 is inserted into a larger sleeve or tube 170 made of a microwave absorbing material. The inner diameter of microwave absorber tube 170 must be large enough as compared to the outside diameter of column 160 to facilitate threading many tens of meters together. The gap should be small enough to keep the interior of the microwave absorber tube 170 at isothermal conditions over the cross-section.

Figure 6:
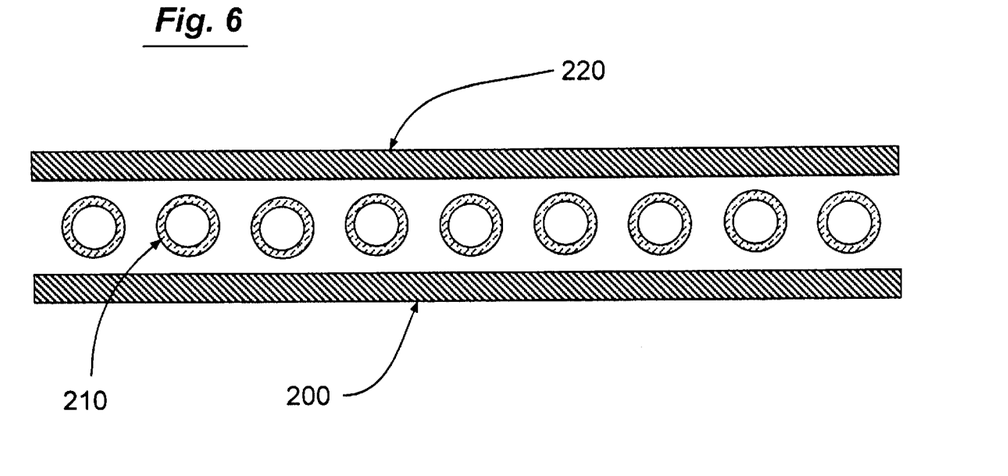
FIGS. 6 and 7 show two different views of a chromatograph column assembly constructed in accordance with the present invention where an existing column is placed adjacent to sheets of microwave absorbing material.
Figure 7:
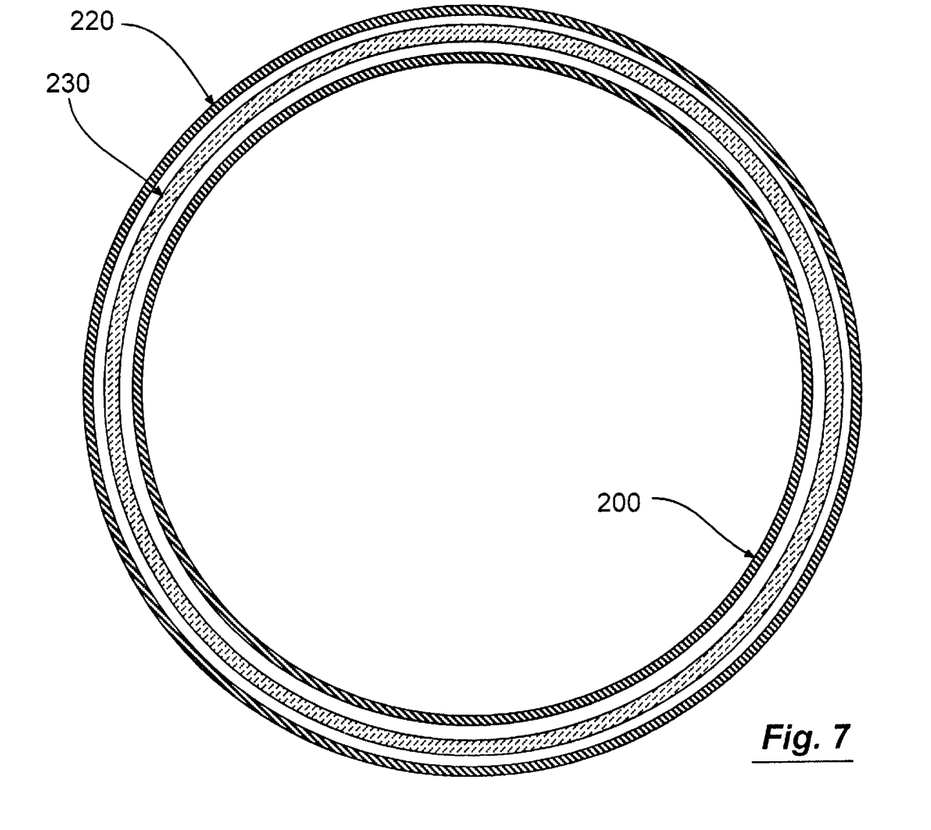

FIGS. 6 and 7 show two views of another column assembly built in accordance with this invention. This assembly is easier to implement than that shown in FIG. 5. Chromatographic columns are often very long and slender— up to 100 meters in length by less than 1 mm in diameter. To make such columns easier to handle, they are usually coiled and held in a spool. An effective column assembly for microwave heating purposes can be constructed by coiling a chromatographic column adjacent to a heating member containing a microwave absorbing material. For example, the column assembly can be constructed by coiling an existing chromatographic column around a core containing a microwave absorbing material. FIG. 6 shows the cross section of such an assembly. FIG. 6 highlights several adjacent column sections 210 sandwiched between two layers 200 and 220 containing a microwave absorbing material. The sandwich can help maintain more stable thermal conditions at different points along the column. FIG. 7 shows a side view of the column assembly. A loop of the column 230 is coiled around a sheet 200 containing a microwave absorbing material. A second microwave absorbing sheet 220 is wrapped outside the column 230. The column 230 and the microwave absorbing sheets 200 and 220 are in effect the concentric cylinders slipped together. If only one microwave absorbing sheet is used instead of two, it could be positioned either inside or outside the column coil. The chromatography column can also be coiled inside a container made of a microwave absorbing material.

It should be understood that the column can be placed adjacent to the heating member containing a microwave absorbing material in any of a number of possible configurations. For example, the column can be placed directly in contact with the microwave absorbing material, or placed adjacent to the microwave absorbing material to provide adequate heat transfer.

There are many different possible assemblies of microwave absorbing materials and chromatographic columns that will keep the column in proximity to the heating member such that the column is heated indirectly by the absorbing material in a microwave heating apparatus. It should be clear to one of average skill in the art that the invention lies in combining a microwave absorbing material and a chromatographic column in an assembly that makes microwave heating possible and not in the specific physical configuration of the assembly.

Microwave absorbing materials used in chromatographic column or column assemblies built in accordance with this invention must have dielectric or magnetic loss factors that are high enough to make microwave heating feasible. Dielectric and magnetic loss factors are often temperature dependent. This characteristic can be utilized to design column assemblies that can only be heated in a microwave heating apparatus to a target temperature and no higher. This design feature can prevent over-temperature conditions that can damage or destroy a column.

Intrinsic over-temperature protection is achieved by selecting a microwave absorber for which the dielectric or magnetic loss factor decreases rapidly at temperatures approaching the maximum desired use temperature of the chromatographic column. As the loss factor of the selected microwave absorber decreases with increasing temperature, the rate at which it absorbs energy in a microwave heating apparatus will also decrease. At some critical point, the temperature will stabilize at a fixed value. This mechanism is illustrated in FIGS. 8 and 9.

Figure 8:
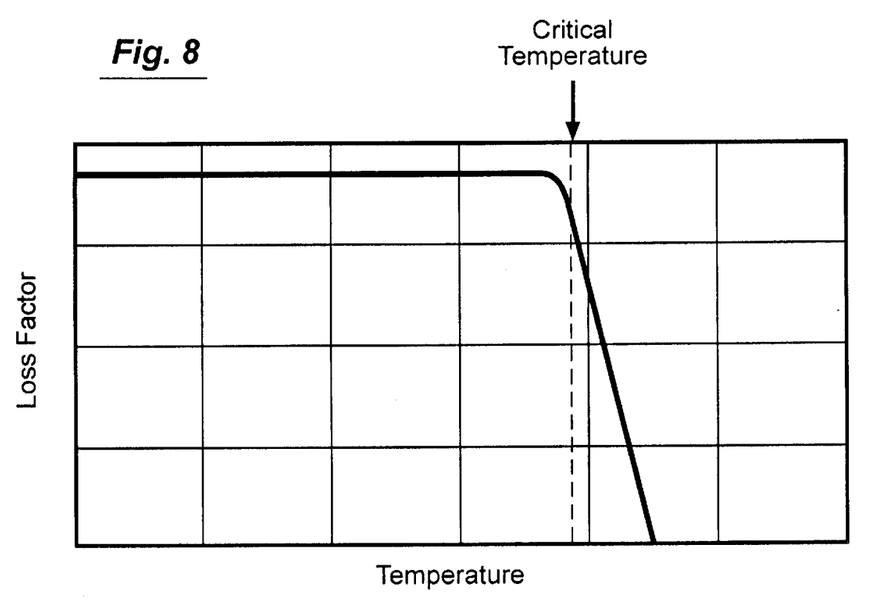
FIG. 8 is a graph illustrating the loss factor of a microwave absorbing material that could be used to limit the maximum temperature to which a chromatographic column assembly built in accordance with this invention can be heated in a microwave heating apparatus.

FIG. 8 shows the loss factor as a function of temperature for a microwave absorbing material that could be used to give a chromatographic column intrinsic over-temperature protection. The loss factor is stable at lower temperatures, but decreases rapidly above some critical temperature. In practice, the loss factor of a suitable microwave absorbing material need not be constant at low temperatures as shown in FIG. 8. The loss factor must simply remain high enough for microwave heating to be efficient at temperatures below the critical temperature, but decrease rapidly over a narrow temperature range to a level at which microwave heating is no longer efficient.

Figure 9:
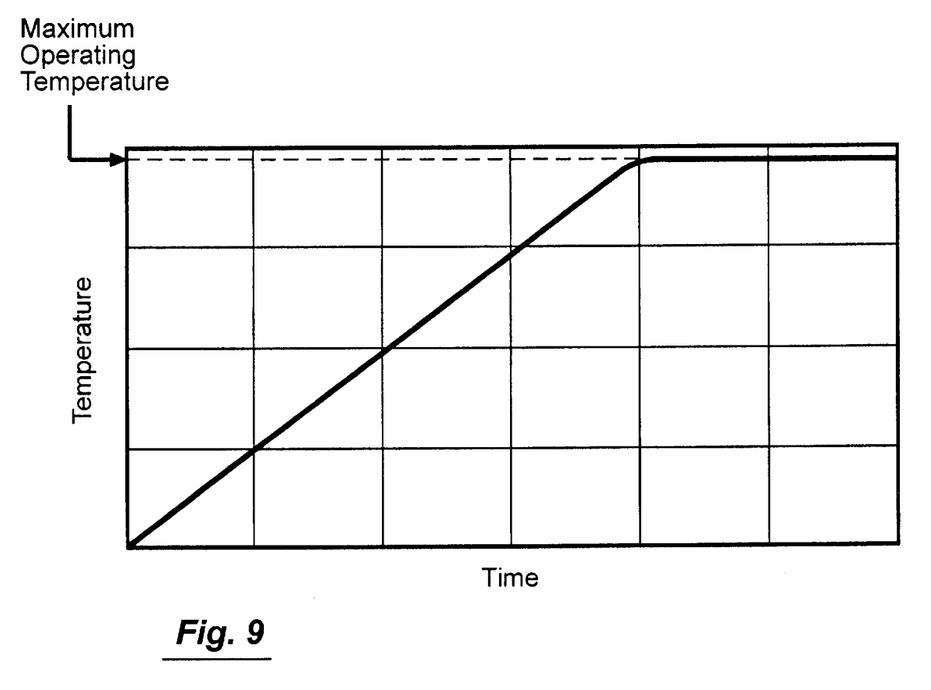
FIG. 9 is a graph showing the heating profile of a column assembly built with intrinsic over-temperature protection in accordance with this invention.

FIG. 9 shows the heating profile for a chromatographic column that is heated in a microwave apparatus where the column is built with a microwave absorbing material that has the loss factor vs. temperature characteristic shown in FIG. 8. At temperatures below the critical loss factor temperature, the rate of temperature increase is substantially constant. At the critical temperature where the loss factor of the microwave absorbing material begins to decrease, the rate of temperature increase slows down. At the temperature at which the heat generated in the microwave absorbing material by the absorption of microwave energy matches the heat lost to the environment, the temperature stabilizes at a fixed value. This temperature is the maximum operating temperature of the column.

Intrinsic over-temperature protection can be achieved by selecting a microwave absorbing material that is ferromagnetic and has an appropriate Curie temperature. The Curie temperature of ferromagnetic materials is the temperature at which they cease to be ferromagnetic and becomes paramagnetic. The Curie temperature also indicates the temperature at which the material's magnetic loss factor approaches zero Thus, a ferromagnetic material cannot be readily heated in a microwave oven beyond its Curie temperatures provided that its dielectric loss factor is also very low. Table 2 shows the Curie temperature of some ferromagnetic materials.

TABLE 2

| Material | Curie Temperature (° C.) |
|---|---|
| Iron | 770 |
| Nickel | 358 |
| Cobalt | 1131 |

Of these materials, nickel is the most suitable for preventing over-temperature conditions in polyimide for which the maximum use temperature is approximately 400° C. Ferrite materials are available with a range of Curie temperatures less than approximately 450° C.

One of the advantages of microwave heating of chromatographic columns over more conventional methods is that thermal energy can be specifically applied to appropriately designed columns or column assemblies and not to the rest of the oven. Because the column or column assemblies have little total material or mass, they also have little thermal mass; therefore, they can be heated or cooled quickly. However, in some circumstances the thermal mass may be so small that heating rates can be compromised by heat lost to the column's environment. Even air surrounding the column may carry away a significant fraction of the thermal energy. An additional problem can arise when cooling the column. If a column is kept at high temperatures for a long period of time, heat loss to the oven environment can eventually raise the temperature of other parts of the oven enough to make quick cooling of the column and the oven difficult. To address these problems, column assemblies built in accordance with this invention can be packaged in a manner which allows the heat flow from the column to be better controlled.

The first element needed to control heat loss from the column is thermal insulation. Columns can be packed in a thermally insulating envelope to minimize the heat loss from them to the rest of the microwave oven. It is not standard practice in the chromatograph business to thermally insulate columns because the columns are heated indirectly in large resistively heated ovens.

Figure 10:
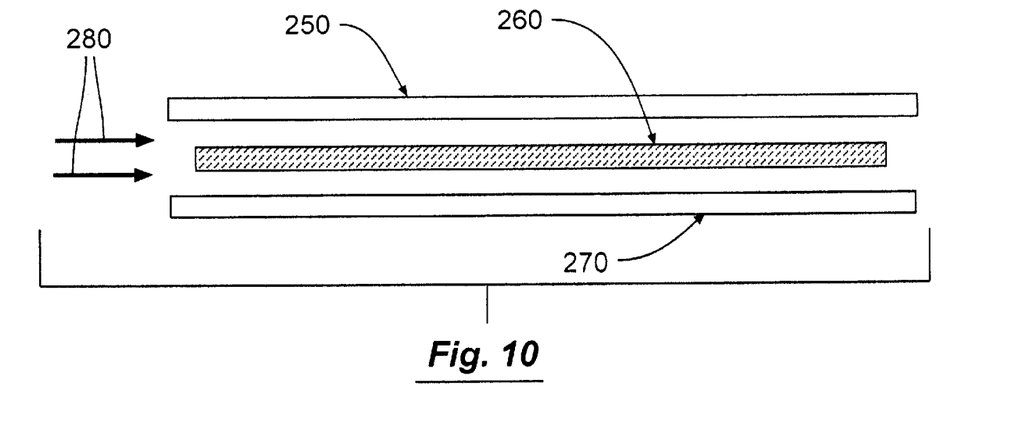
FIGS. 10 and 11 show the cross sections of apparatuses designed to help control the heat loss from column assemblies built in accordance with this invention.

FIG. 10 shows one embodiment of a column insulating system. The perspective in FIG. 10 is the same as in FIG. 6. A column or column assembly 260 built in accordance with this invention is sandwiched between two thermal insulators 250 and 270 which reduce the heat loss from the column to the environment. In a preferred embodiment, the column assembly insulators 250 and 270 are made into concentric cylinders with the column assembly 260 coiled between them. This structure is as shown in FIG. 7. Insulators 250 and 270 need not be the same material and one or the other may be eliminated in some circumstances. A gap can be left between the thermal insulators 250, 270 and the column assembly 260 for ventilation to facilitate rapid cooling of the column assembly 260 after completion of the heating cycle.

Figure 11:
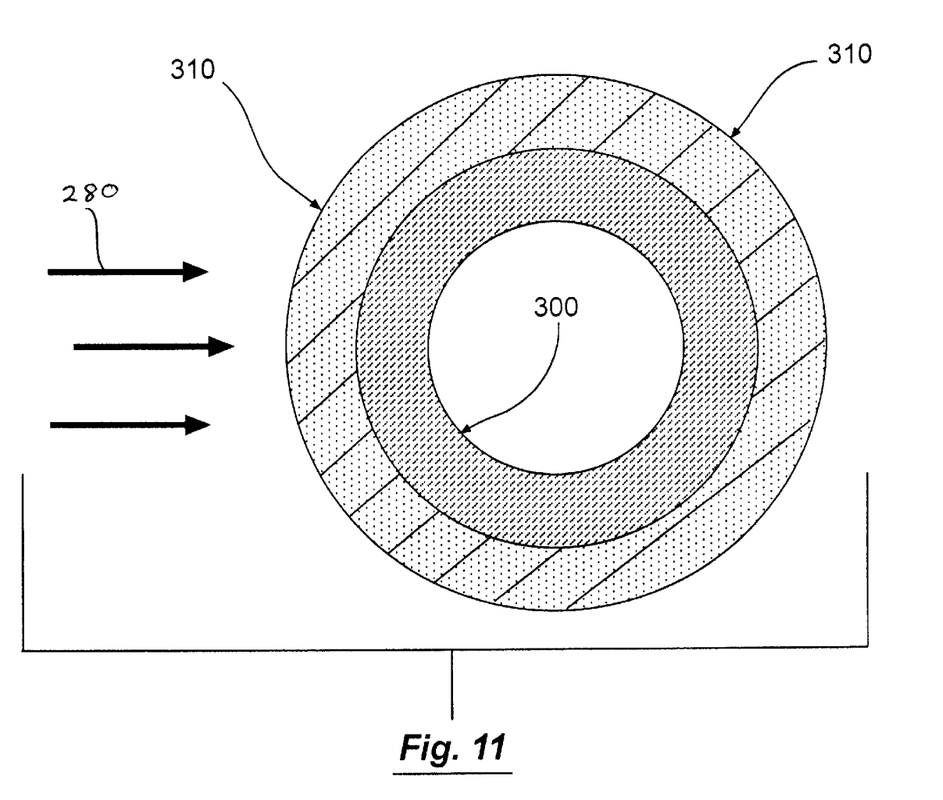

In another preferred embodiment as shown in FIG. 11, a column 300 built in accordance with this invention is sheathed within a layer of thermal insulation 310 that reduces heat loss from the column. If the material layer 100 in FIG. 3 is a good thermal insulator, a separate layer of thermal insulation may not be necessary. As described in reference to FIG. 3, an outer layer of polyimide is attractive because it helps to shield the microwave absorbing material 90 from the environment. As polyimide is a good insulator, it can also help thermally shield the column.

There are many different thermal insulators that could be used in this invention: plastics, ceramics, and fiberglass to name a few. Another possible insulator is a vacuum. If most of the air is pumped out of a microwave heating apparatus so that a column assembly is heated in a vacuum, then very little heat will be lost from the column at useful chromatographic temperatures. The two requirements for the insulation material are that: (1) it must be transparent to high frequency electromagnetic radiation such that it does not shield the column assembly from this radiation and thus prevent the column assembly from heating; and (2) it must have low dielectric and magnetic loss factors so that it will not be heated directly by microwave radiation.

The second element needed to control heat loss from the column is a means for quickly removing the heat from the column or column assembly when cooling is required. In other words, a means of circumventing the thermal insulation and accelerating thermal loss. Accelerated thermal loss is most easily achieved by blowing cool air, a cryogenic gas, or some other convenient material 280 over the column assembly as shown in FIGS. 10 and 11 until the temperature is reduced to the desired level. If the heating process is performed in a vacuum, then blowing cool air through the oven during the cool down cycle will quickly reduce the column temperature to the desired level. If the column assembly is equipped with an outer layer of thermal insulation as depicted in FIG. 10, a blower or ventilation system can be used to induce a flow of air through the gap between the insulation layer and the column to accelerate cooling after completion of each heating cycle.

Conductivity Limits in Columns or Column Assemblies Heated with Microwaves. Materials with high electrical conductivity, such as metals, tend to short out or significantly distort the electromagnetic field within microwave heating apparatuses thus preventing normal microwave heating. However, the electromagnetic field is only distorted significantly if a high conductivity path extends for some length parallel to the electric field. Thus, a metal wire or sheet will not disturb the electric field in a microwave heating apparatus if the sheet or wire is placed in the heating apparatus in a position that is essentially perpendicular to the electric field lines in the heating apparatus. The reason for this is that significant electric currents are not induced in a metal wire by an electric field that is perpendicular to the wire. This behavior can affect the design of columns or column assemblies to be heated in microwave heating apparatuses.

Microwave absorbing material must be added to a column or column assembly in order to heat them in microwave heating apparatuses. Many microwave absorbing materials or matrices are least partly conductive electrically. Carbon-loaded polyimide can be quite conductive for example. The conductivity of microwave absorbing materials or matrices used to heat chromatographic columns in microwave heating apparatuses must not be too high. The upper conductivity limit depends upon the orientation of the microwave absorbing material with respect to the electric field within a given microwave heating apparatus.

Figure 12:
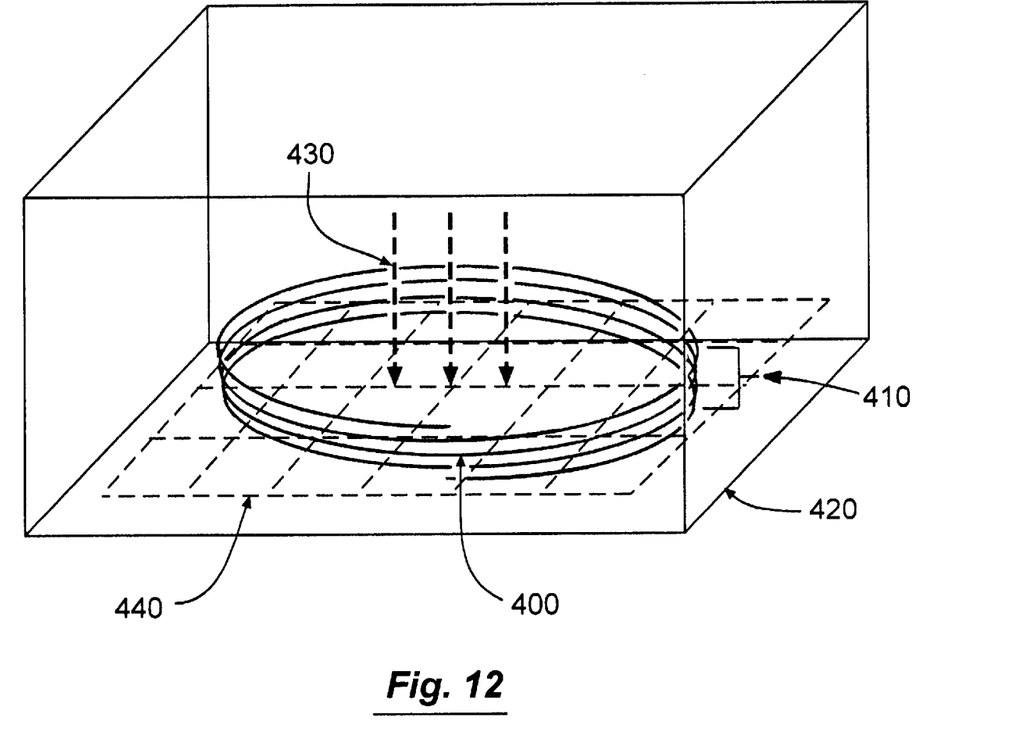
FIG. 12 shows a column configuration in which the microwave absorbing material is essentially perpendicular to the direction of the electric field in a microwave heating apparatus.

A microwave absorbing material oriented essentially perpendicular to the electric field in a microwave heating apparatus has no significant electrical current path length parallel to the electric field. An example of such a structure is shown in FIG. 12. A column 400 with a microwave absorbing material coated on the outside as shown in FIG. 2 is coiled into a circular column bundle 410. The column bundle 410 is placed in a microwave heating apparatus 420 in which the electric field 430 is perpendicular to the plane 440 of each loop of the column bundle 410. When the electrical current path in a microwave absorbing material used to heat a column or column assembly is essentially perpendicular to the electric field in a microwave heating apparatus, the volume conductivity of the microwave absorbing material can be as high as approximately 5000 mho/cm. Conversely, if the microwave absorbing material is positioned in a microwave heating apparatus such that there is a conductivity path of sufficient length (greater than 2% of the free space wavelength) that is parallel to the electric field, then the maximum conductivity of the microwave absorbing material is approximately 100 mho/cm.

The above disclosure sets forth a number of embodiments of the present invention. Specifically, the above disclosure addresses capillary and packed chromatographic columns designed to be heated by a microwave heating apparatus. Other arrangements or embodiments, not precisely set forth, could be practiced under the teachings of the present invention and as set forth in the following claims.

We claim:

1. A chromatography column for heating in a microwave heating apparatus, said chromatography column comprising:
   a continuous phase material forming a wall surrounding an interior space for containing a chromatography sample; and
   a microwave absorbing material contained in said continuous phase material;
   wherein said chromatography column has a loss factor sufficient to absorb at least approximately 50% of the microwave energy transmitted into the microwave heating apparatus.

2. The chromatography column of claim 1 wherein said continuous phase material comprises fused silica.

3. The chromatography column of claim 1 wherein said wall comprises a composite of said continuous phase material and said microwave absorbing material.

4. The chromatography column of claim 1 further comprising a layer of thermal insulation surrounding said microwave absorbing material.

5. A chromatography column for heating in a microwave heating apparatus, said chromatography column comprising:
   an inner layer for holding a sample; and
   an outer polymer layer surrounding said inner layer containing a microwave absorbing material, wherein said outer layer has a loss factor sufficient to absorb at least approximately 50% of the microwave energy transmitted into the microwave heating apparatus.

6. The chromatography column of claim 5 wherein said inner layer comprises fused silica.

7. The chromatography column of claim 5 wherein said outer polymer layer comprises a composite of polyimide and said microwave absorbing material.

8. The chromatography column of claim 5 wherein said microwave absorbing material is selected from the group consisting of ferrite, iron, cobalt, nickel, and carbon.

9. The chromatography column of claim 5 wherein said microwave absorbing material has a temperature-dependent loss factor providing a predetermined maximum temperature for heating said chromatography column.

10. The chromatography column of claim 5 wherein said microwave absorbing material has a Curie temperature less than approximately 450° C.

11. The chromatography column of claim 5 further comprising a layer of thermal insulation surrounding said outer polymer layer.

12. The chromatography column of claim 11 further comprising a gap between said outer polymer layer and said layer of thermal insulation.

13. A chromatography column assembly for heating in a microwave heating apparatus, said chromatography column assembly comprising:

a heating member containing a microwave absorbing material having a loss factor sufficient to absorb at least approximately 50% of the microwave energy transmitted into the microwave heating apparatus; and a chromatography column coiled adjacent to said heating member for heating said chromatography column.

14. The chromatography column assembly of claim 13 wherein said heating member comprises a plurality of layers containing said microwave absorbing material, and wherein said chromatography column is sandwiched between said layers.

15. The chromatography column assembly of claim 13 wherein said heating member comprises a core containing said microwave absorbing material, and wherein said chromatography column is wrapped around said core.

16. The chromatography column assembly of claim 13 wherein said heating member comprises a container made of said microwave absorbing material, and wherein said chromatography column is coiled inside said container.

17. The chromatography column assembly of claim 13 further comprising a layer of thermal insulation surrounding said chromatography column and said heating member.

18. The chromatography column assembly of claim 17 further comprising a gap separating said chromatography column and said layer of thermal insulation.

19. The chromatography column assembly of claim 13 wherein said microwave absorbing material has a temperature-dependent loss factor providing a predetermined maximum temperature for heating said chromatography column assembly.

20. The chromatography column assembly of claim 13 wherein said microwave absorbing material has a Curie temperature less than approximately 450° C.

* * * * *